US009095368B2

(12) United States Patent
Umar et al.

(10) Patent No.: US 9,095,368 B2
(45) Date of Patent: Aug. 4, 2015

(54) FOLLICULAR UNIT EXTRACTION DEVICE

(75) Inventors: Sanusi Umar, Redondo Beach, CA (US); Robert Evans, Pasadena, CA (US)

(73) Assignee: Sanusi Umar, Redondo Beach, CA (US)

( * ) Notice: Subject to any disclaimer, the term of this patent is extended or adjusted under 35 U.S.C. 154(b) by 137 days.

(21) Appl. No.: 13/885,254

(22) PCT Filed: Apr. 20, 2012

(86) PCT No.: PCT/US2012/034571
§ 371 (c)(1),
(2), (4) Date: May 14, 2013

(87) PCT Pub. No.: WO2012/145710
PCT Pub. Date: Oct. 26, 2012

(65) Prior Publication Data
US 2014/0031839 A1    Jan. 30, 2014

Related U.S. Application Data (60) Provisional application No. 61/477,233, filed on Apr. 20, 2011, provisional application No. 61/603,525, filed on Feb. 27, 2012.

(51) Int. Cl.
*A61B 17/50* (2006.01)
*A61B 17/3205* (2006.01)
(Continued)

(52) U.S. Cl.
CPC ......... *A61B 17/32053* (2013.01); *A61B 17/322* (2013.01); *A61B 2017/00752* (2013.01)

(58) Field of Classification Search
CPC ............. A61B 10/266; A61B 10/0283; A61B 17/32053; A61B 2017/00752; A61B 17/3468; A61B 2017/00969
See application file for complete search history.

(56) References Cited

U.S. PATENT DOCUMENTS 5,817,120 A * 10/1998 Rassman ........................ 606/187
5,827,297 A    10/1998 Boudjema
(Continued)

FOREIGN PATENT DOCUMENTS

WO       91/13596 A1    9/1991

OTHER PUBLICATIONS

Written Opinion of the International Search Authority; PCT US12/34571 (from which this is an application under 35 USC 371).
(Continued)

*Primary Examiner* — Jonathan W Miles
(74) *Attorney, Agent, or Firm* — Law Office of Michael O'Brien (57) ABSTRACT

A follicular unit extraction device comprises a handpiece for holding a follicle punch at its distal end which extends from the handpiece and terminates distally in a cutting edge. The punch is releasably coupled to a motor-driven drive shaft within the handpiece for rotation therewith. A portion of the driveshaft is tubular, and houses a piston that can move towards and away from the punch. An ejector pin is also supported within the tubular portion of the driveshaft distally of the ejector piston and is positioned to move towards the cutting edge of the punch when pushed by the piston. The handpiece and driveshaft have respective fluid inlet ports. The clearance between the piston and driveshaft interior, and the clearance between the ejector pin and punch interior, define a fluid path for conducting fluid entering the handpiece and drive shaft via inlet ports so that the fluid exits the punch at its cutting edge. The clearances limit the quantity of fluid exiting the punch to the small amount needed to protect the follicle to be extracted. Means are provided for selectively increasing the flow rate of the fluid entering the handpiece beyond the limit imposed by said clearances to thereby increase the fluid pressure within the driveshaft, moving the piston distally and, consequently, moving the pin towards the cutting edge of the punch to eject impacted graft or debris. Bias means returns the piston proximally when the flow rate is reduced below the level required to overcome the bias means.

10 Claims, 5 Drawing Sheets

(51) Int. Cl.
*A61B 17/322* (2006.01)
*A61B 17/00* (2006.01)

(56) References Cited

U.S. PATENT DOCUMENTS

| | | | |
|---|---|---|---|
| 6,059,807 A | 5/2000 | Boudjema | |
| 7,144,406 B2* | 12/2006 | Pak et al. | 606/187 |
| 2003/0097144 A1* | 5/2003 | Lee | 606/187 |
| 2005/0096687 A1* | 5/2005 | Rassman et al. | 606/187 |
| 2005/0187573 A1* | 8/2005 | Rassman et al. | 606/187 |
| 2008/0051816 A1* | 2/2008 | Pak et al. | 606/187 |
| 2010/0030234 A1 | 2/2010 | Bodduluri | |
| 2010/0125287 A1 | 5/2010 | Cole | |

OTHER PUBLICATIONS

Extended European Search Report; Jan. 9, 2015 (sic); EP Patent Application No. 12774153.6.
International Preliminary Report on Patentability; Mar. 7, 2013; PCT US12/34571 (from which this is an application under 35 USC 371) (pp. 4-18).

* cited by examiner

FOLLICULAR UNIT EXTRACTION DEVICE

BACKGROUND OF THE INVENTION

Follicular Unit Extraction ("FUE") is a surgical hair transplantation technique that involves moving skin containing hair follicles from one part of the body (the donor site) to bald or balding parts (the recipient site). Hair naturally grows in follicles that contain groupings of 1 to 4 hairs, and the transplant technique typically moves the 1-4 hair "follicular units" from the donor site to the recipient site.

The follicle units (sometimes referred to as "grafts") are typically removed from the donor site using punches of between 0.7 mm and 1.25 mm in diameter. The punches are typically tubular bodies having a skin-contacting cutting edge, and are typically mounted in a hand-held electric-powered tool that causes the punch to rotate or oscillate as the cutting device is brought into contact with the donor site, but are sometimes used manually.

Hair follicles are very easily broken during the removal, and broken follicles are unlikely to be successfully transplanted. One of the major causes of low yield in FUE is attributable to desiccation forces imparted on the graft following its dissection from its tissue investiture; more specifically, as it is pulled from the donor site, and as it is placed in a physiological holding solution such as normal saline, ringer's lactate, etc. for subsequent transplantation at the recipient site.

One known FUE device even uses a suction mechanism to suck out the graft immediately following desiccation and propel it pneumatically through a tube into a collection canister that contains a physiological medium. The sucked graft is subjected to traumatic forces as it is funneled at high force and velocity out of the donor site and through the narrow tube, banging against the tube wall as it is propelled to the canister. Additionally, sucking and pulling the graft as it is cut from the donor site creates a risk of transection from the combined vectors of pulling and rotating as the rotating cutting device creates a like rotation in the graft being extracted while it is tethered to the surrounding tissue at the donor site. Moreover, the suction effect strips the graft of some of its protective tissue investiture, further diminishing its protection from damaging desiccating factors as well as trauma.

SUMMARY OF DESCRIPTION

An FUE device constructed in accordance with the invention is directed to the elimination of, or at least a substantial reduction in, the desiccation forces to which extracted follicle units are subjected during the extraction process to thereby increase the yield of successfully transplantable follicles harvested from the donor site. The FUE device comprises a handpiece configured to securely hold a follicle punch, and utilizes fluid irrigation and a pumping mechanism whereby fluid is delivered to the cutting edge of the punch during the cutting and extraction of the follicle unit. In its preferred embodiment, the fluid is delivered through the punch's lumen. As an additional feature, the fluid is selectively delivered in greater quantity through the punch lumen to clear impacted follicles and/or debris from the punch The fluid can be carried to the cutting edge in any of a number of ways. For example, it can be delivered through the lumen of the punch and directed outwardly towards the cutting edge at the skin-contacting end of the punch or delivered to the punch via a conducting path external to the punch.

Any of a number of fluids can be used, including physiologic or other solutions, and may also be a fluid that may or may not have been proven to prolong or sustain graft or tissue viability.

In addition, the handpiece is preferably configured to cause punch rotation during at least the cutting phase of the extraction process.

THE DRAWING

For visual clarity, like reference numerals have been used throughout the Figures to denote corresponding components, although some corresponding components may have described or illustrated modifications.

DETAILED DESCRIPTION OF PREFERRED EMBODIMENT

One embodiment of the FUE device maintains a continuous drip of variable rate that creates and sustains a fluid film around the partially or completely separated graft to protect the exposed tissue around the graft from ambient desiccation factors, including air. These desiccating factors contribute to low viability of the grafts during the period between its dissection from the surrounding tissue at the donor site and its placement in the physiological medium. Further, the fluid in the punch lumen, serves as a lubricant that reduces the friction between the graft and the internal wall of the punch thereby reducing the twisting of the upper portion of the follicle which has been partially or wholly dislodged from its surrounding tissue attachments. This serves to further reduce the transection rate.

The delivered fluid also creates a moist skin surface around the targeted follicle, presenting a smoother surface against which the cutting end portion of the punch glides for a cleaner cut than a dry surface as well as a reduction in friction-generated shearing force by the rotating punch on the follicle.

In addition, the reduced friction experienced by the cutting edge of the punch results in a lesser dulling effect on the cutting edge and a consequential increase in the life of the punch.

The flow rate of the fluid can be controlled automatically via a digit or analog control circuit, by computer control and/or or by a manually rotated dial or slider or button mechanism located either in the handpiece of the rotary tool or in a control box near the patient, or by foot control. The flow rate can be controlled by wired or by wireless communication/control technology. The handpiece may or may not be autoclavable by heat or immersion, either in whole or in parts.

Figures 1, 2A, 2B, 3:
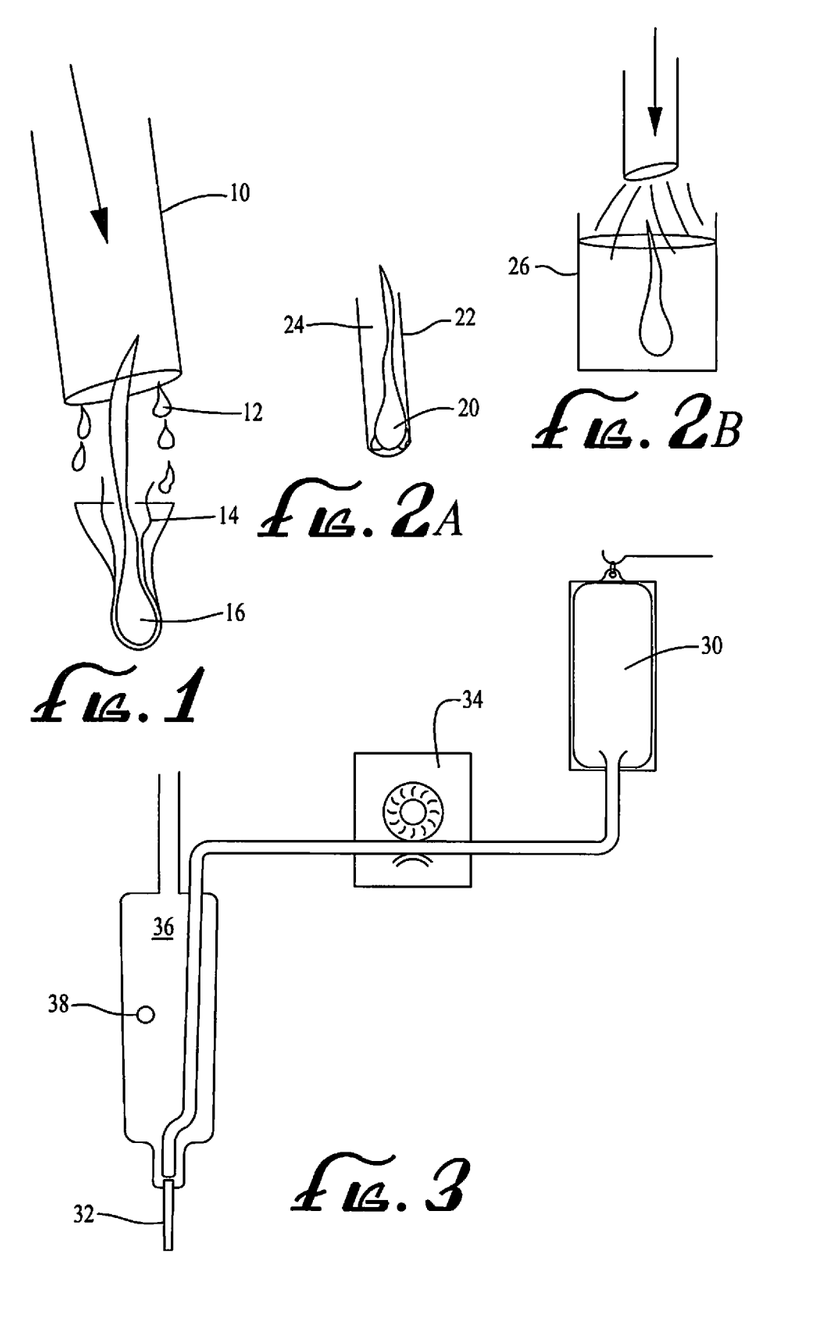
FIG. 1 is a sketch of a front elevation view in schematic illustrating the skin-contacting edge of a follicle punch to which fluid is being delivered in accordance with the invention.
FIGS. 2A and 2B are sketches of front elevation views in schematic illustrating an intact graft impacted within the lumen of a follicle punch, and being ejected into a receptacle in accordance with the invention.
FIG. 3 is a sketch in schematic of an FUE system constructed in accordance with the invention.

As illustrated by way of example in FIG. 1, fluid droplets 12 exiting from the region of a punch 10 near the cutting edge have formed a fluid film 14 around a follicle unit 16 at a donor site.

A variation of the foregoing embodiment employs a fluid conduit external to the punch to direct the fluid to the cutting edge.

A second variation of the FUE device provides an additional pulsed application of the fluid through the lumen of the punch at a sufficiently high pressure to push out any graft or tissue debris, enabling the graft or tissue debris to be ejected into a receptacle. This services several purposes. First, it addresses the current need to interrupt the dissection and removal procedure at the donor site to clean out the punch's lumen when the lumen becomes impacted with debris. The application of pulsed fluid through the lumen reduces and minimizes the interruption. The term "pulsed" includes, within its scope, one or more pulses of predetermined or user-determined length which raise the pressure sufficiently to push out the graft or debris.

Second, an intact graft that gets completely separated from its surrounding tissue by the punch may be impacted within the lumen of the punch close to the cutting tip. When this occurs, work must conventionally be interrupted in order to manually extract and salvage the impacted graft and continue the work. Again, the application of pulsed fluid through the lumen to eject the impacted graft reduces and minimizes the interruption of the procedure and provides a means for salvaging the graft with minimal chance of desiccation while saving a considerable amount of time.

FIG. 2 illustrates an example of the foregoing. An impacted graft 20 (FIG. 2A) within a punch 22 is subjected to a pressurized fluid 24 variation, and is expelled (FIG. 2B) into a container 26 of physiological fluid.

Figure 4:
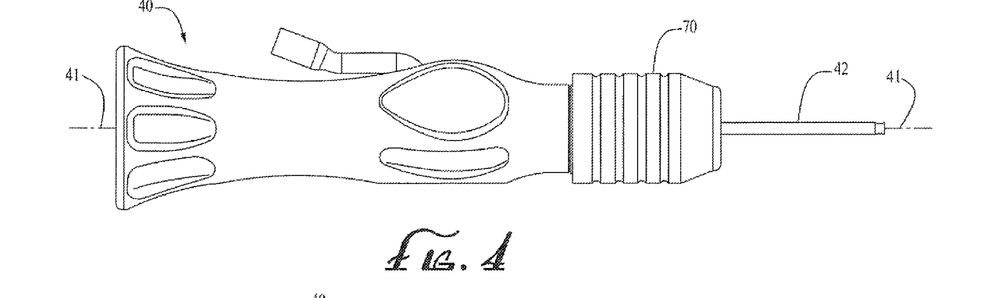
FIG. 4 is a side view of a an FUE handpiece constructed in accordance with the invention.
Figure 5:
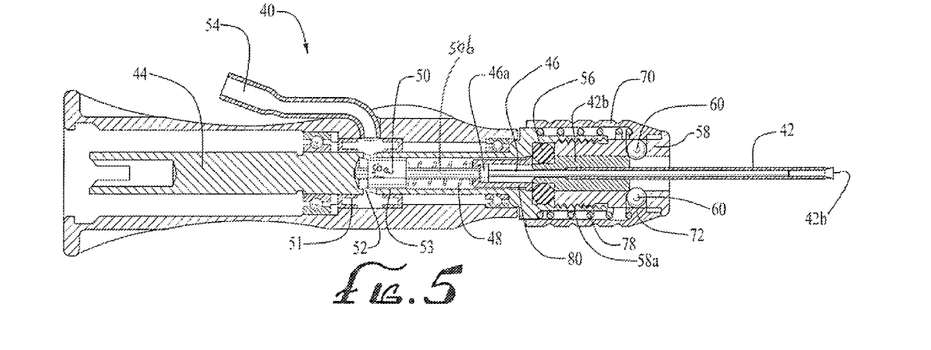
FIG. 5 is a longitudinal sectional view of the handpiece and follicle punch in the orientation shown in FIG. 4.

A third variation, which is the currently preferred configuration, is exemplified in FIGS. 4 and 5, and utilizes a mechanical component to push out any graft or tissue debris. The illustrated and currently preferred mechanical component includes a pin 46, described hereinafter in more detail.

The fluid reservoir from which the delivered fluid is taken may be remote from the device and located separately in a drip stand, for example, as shown in FIG. 3 at 30, or it may be integral with the control box 34 (if one is used) or some other part of the device.

The hardware by which the fluid is pumped towards the cutting edge may include an electro-mechanical pump, a gravity system or a manual or other mechanical pump without departing from the intended scope of the invention. The hardware can be controlled manually or be computer-controlled.

FIG. 3 illustrates an example of the foregoing. Physiological fluid is delivered from a bag 30 to a follicle punch 32 via a rate controller 34. The punch 32 is held by a handpiece 36 that is provided with a pump-controlling button 38 by which the fluid can be caused to pulse at a pressure sufficient to dislodge the impacted follicle and/or debris.

FIG. 4 is a side view of a preferred FUE handpiece 40 constructed in accordance with the invention wherein the preferred mechanical component is utilized to clear the follicle punch of impacted follicles and/or debris, and FIG. 5 is a sectional view of the handpiece in the orientation shown in FIG. 4. The preferred handpiece 40 comprises a generally cylindrical body, with an ergonomically contoured exterior, extending along a generally central axis 41. The handpiece holds a follicle punch 42 that is coupled to a motor-driven driveshaft 44 within the handpiece for rotation about axis 41. An ejector pin 46 is positioned within the handpiece for axial movement within the follicle punch to eject an impacted graft from the punch's interior. To eject the impacted graft, the ejector pin is urged forward axially into the punch. In the illustrated embodiment, the ejector pin 46 is urged forward axially into the punch, against the force of a return spring 48, by an ejector piston 50 in response to a build-up of fluid pressure behind the piston. The fluid is introduced behind the piston through ports 52 within the handpiece. As described in greater detail below, the fluid is preferably an irrigation liquid, such as a suitable sterile saline solution that is also applied to the donor site by the handpiece. Accordingly, the preferred liquid is introduced into the handpiece via an inlet conduit 54 that is, in turn, fluidically coupled to the content of a container of irrigation fluid (not illustrated).

It will be understood that the ejector pin can alternatively be moved mechanically, electrically or magnetically instead of hydraulically. For example, the pin can be mechanically linked to a slider mechanism or other contact surface that is manually actuated by the user. The pin can thereby be manually moved forward or both forward, or can be mechanically urged forward against a return spring or other biasing means so that the rod moves away from the cutting end upon the user's release of the slider mechanism or other contact surface. Alternatively, the pin can be linked to the slider mechanism (or other contact surface) magnetically rather than mechanically.

The piston 50 and the pin 46 may be integrally formed as a single piece, but this is not preferred. The pin 46 is very thin (e.g., 0.025 inches (0.635 mm) in diameter) and delicate. When the punch is removed from the handpiece to be changed, an integrated pin would extend from the handpiece without substantial support and could easily be bent. If bent, the pin will not move freely within the punch, if at all. Even if not bent, the extending pin would require the new punch to be carefully mounted to the handpiece to avoid damaging the rod, making its attachment to the handpiece more difficult. By maintaining the pin separate from the piston, the pin can be removed from the handpiece with the punch, and place within the new punch just prior to its mounting to the handpiece, permitting the punches to protect the integrity of the rod. As used herein, the term "piston" will accordingly include the portion of the integrated component functioning as the piston, ands the terms "rod" and "ejection rod" will include the portion of the integrated component functioning as the pin unless the context of the usage clearly denotes otherwise.

Figure 6:
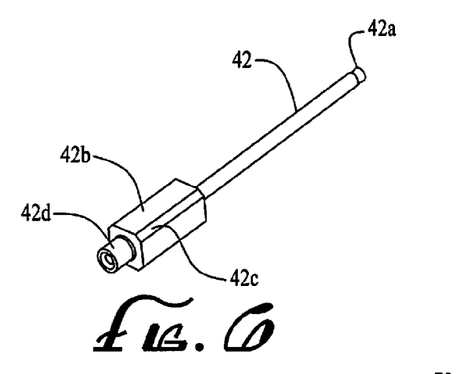
FIG. 6 is a perspective view of a follicle punch assembly constructed in accordance with the invention.

FIG. 6 is a perspective view of the preferred follicle punch assembly illustrated in FIG. 5. It comprises a generally tubular follicle punch 42 having a cutting edge 42a and a coupling block 42b. The coupling block can be formed integral with the punch, but it is preferred that that it be pressed-fit or welded onto the punch. The coupling block is provided with an exterior shape that, as will be seen, is securely engaged by the handpiece for rotation. In the illustrated embodiment, and as best shown in FIG. 6, the coupling block is an elongated tubular body of generally square cross-section, and is beveled at diagonally opposite corners 42c (of which one such corner is hidden in the view of FIG. 6) to provide the desired engagement. Many other possible shapes will be apparent to those of ordinary skill in the art.

The rear portion, or nub, 42d of the follicle punch assembly is generally cylindrical, and is preferably manufactured as part of the block. As illustrated in FIG. 5, the rear portion 42d fits within a sealing ring 56 in the handpiece, while the coupling block 42b is engaged within a driver socket 58. The preferred driver socket 58 in this embodiment is illustrated more clearly in FIG. 7, and is a generally tubular component having a threaded rear end portion 58a, a front portion 58b of relatively larger outside diameter, an axially-extending through-hole 58c and a pair of radially-extending holes 58d formed in its mid-portion therebetween. The axially-extending through-hole 58c is shaped to firmly engage the coupling block 42b when the punch assembly is mounted within the driver socket 58; accordingly, the preferred cross-section of the illustrated through-hole is square and sized to securely engage the coupling block.

Figure 9:
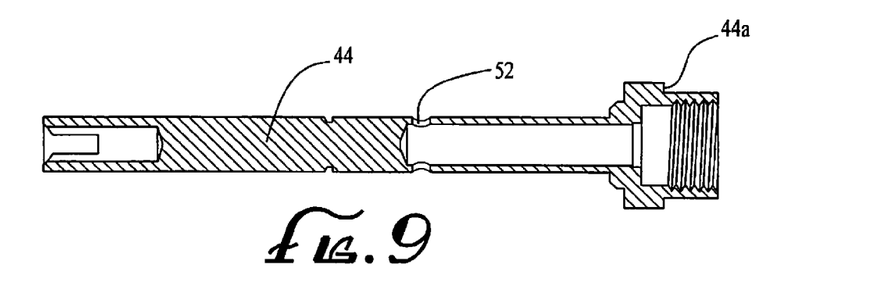
FIG. 9 is a longitudinal sectional view of the driveshaft 44 shown in FIG. 5.

As illustrated in FIG. 5, the threaded end 58a of the driver socket 58 mates with the internally-threaded end region 44b of the drive shaft 44, shown more clearly in FIG. 9. As also illustrated in FIG. 5, two steel balls 60 nest within the radially-extending holes 58d of the drive socket (FIG. 7) and are pressed into releasable engagement with the beveled surfaces 42c of the coupling block 42b (FIG. 6) as described below to function as a detente. Preferably, the balls extend over the corners on opposite flat sides to keep the block 42b in.

Figure 8:
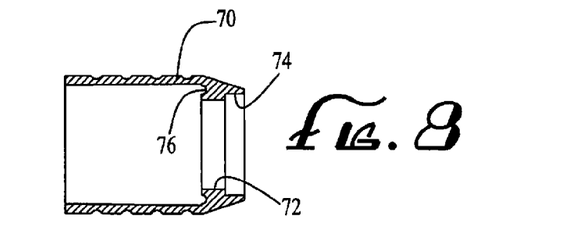
FIG. 8 is an enlarged view of the chuck sleeve 70 illustrated in section in FIG. 5.

The balls 60 are pressed into the holes 58d by a radially-protruding inner shoulder 72 of a chuck sleeve 70 (FIGS. 4-5, 8). The chuck sleeve can be slid axially rearward against a spring 78 to disengage the balls from the shoulder 72 and thereby permit removal of the follicle punch assembly 42 from the handpiece as the balls slide or roll along the beveled corners 42c (FIG. 6) of the punch assembly. Preferably, the balls slide along the flats. The spring 78 is captured between the inner shoulder 72, at region 76, and a radially outwardly-projecting shoulder 44a of the driveshaft 44 (best seen in FIG. 9). The spring 78 is compressed as the chuck sleeve 70 is slid axially rearward, and returns the sleeve to the punch-securing position illustrated in FIG. 5 when released by the user.

Figure 7:
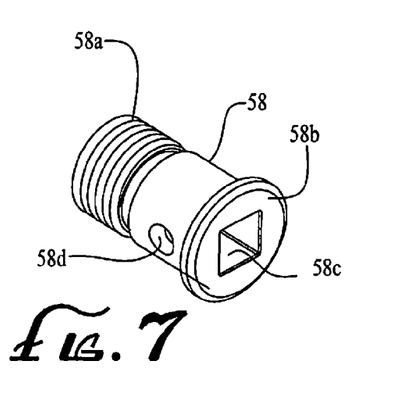
FIG. 7 is a front left perspective view of the drive socket 58 illustrated in FIG. 5.
Figures 12, 13, 14, 15:
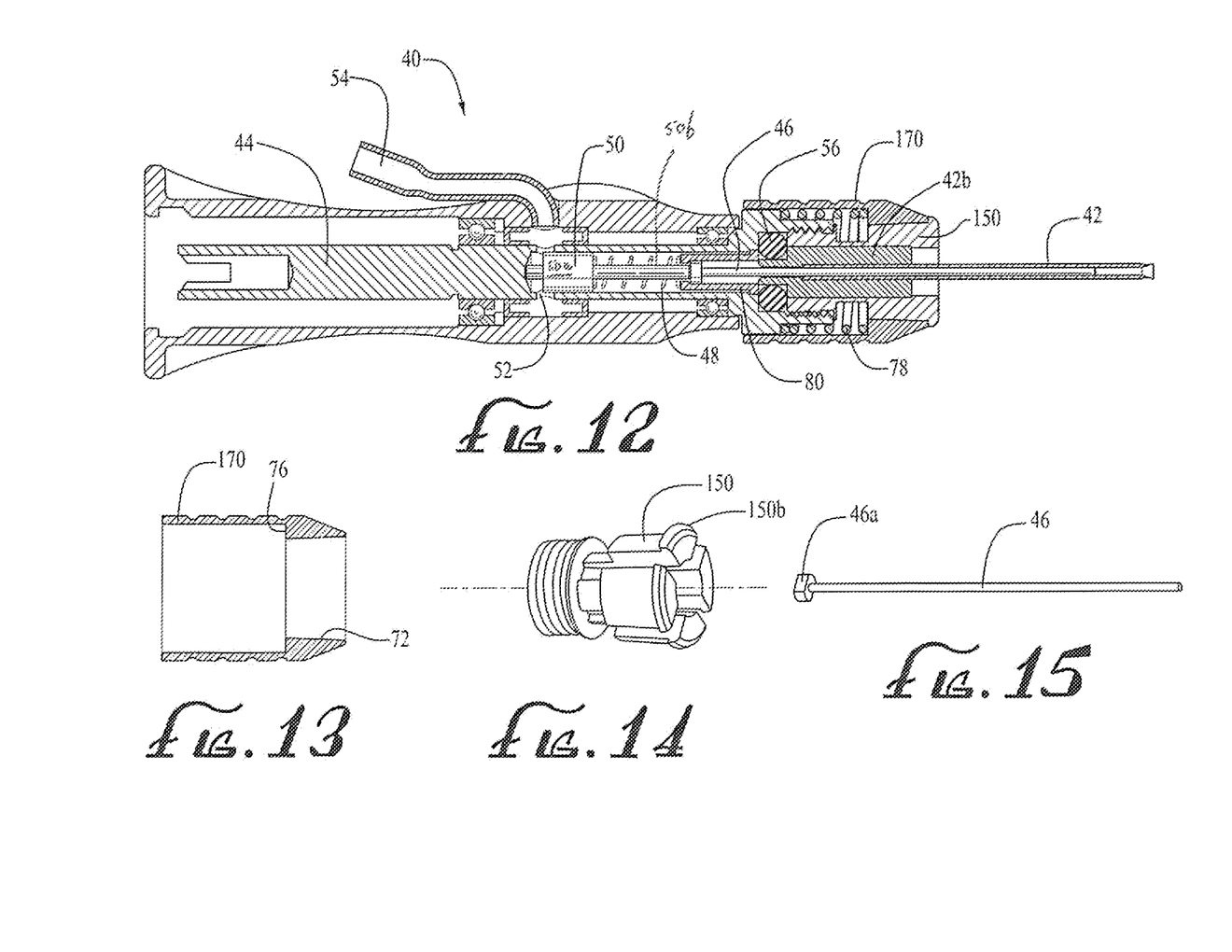
FIG. 12 is a longitudinal sectional view of an alternative embodiment of a handpiece constructed in accordance with the invention and in the orientation shown in FIG. 4.
FIG. 13 is an enlarged view of the preferred chuck sleeve used in connection with the embodiment of FIG. 12.
FIG. 14 is a side view of the collet 150 illustrated in FIG. 12.
FIG. 15 is a side view of the preferred ejection pin 46 illustrated in FIGS. 5, 12 and 16.

An alternative punch-engaging structure is illustrated in FIGS. 12 and 13, which are respectively similar to FIGS. 5 and 8, and in FIG. 14 which illustrates the component corresponding to that in FIG. 7. In this alternative, a collet arrangement is used to secure the punch within the handpiece. Accordingly, one or both of the inter-engaging surfaces of the driver socket 150 and sleeve 170 are provided with a taper, with the driver socket being formed as a collet. Accordingly, the OD of the illustrated driver socket's interengaging region 150b and the ID of the illustrated sleeve are dimensioned so the collet expands slightly as the sleeve 170 is slide rearwardly (i.e., away from the cutting end of the illustrated punch 42), releasing its grip on the punch. Conversely, a punch can be inserted into the driver socket 150 while the sleeve is in its rearward position, and the collet of the driver socket will be compressed radially inwardly by the ID of the sleeve as the spring 78 urges the sleeve forward upon the user's release of the sleeve. Those of ordinary skill in the art will recognize that other interengaging surface configurations can be used and are within the scope of the invention.

Figure 10:
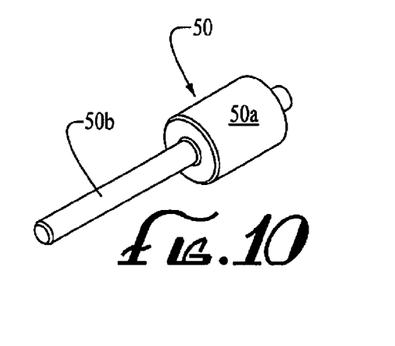
FIG. 10 is a front right perspective view of the ejector piston 50 illustrated in FIG. 5.

As described earlier with respect to FIG. 5, the ejector pin 46 is positioned within the handpiece for axial movement within the follicle punch to eject an impacted follicle unit from the punch's interior. To eject the impacted follicle unit, the ejector pin is urged axially forward into the punch, against the force of a return spring 48, by an ejector piston 50, best illustrated in FIG. 10. As illustrated in FIG. 10, the preferred piston comprises a generally cylindrical piston head 50a and a forwardly-extending rod portion 50b of comparatively smaller diameter. As illustrated in FIG. 5, the rod portion sized to move axially forward within a piston guide 80 to push an impacted follicle unit out of the cutting end of the punch with the pin 42. An approximately 0.060 inch protrusion on the backside of the piston keeps the back side of the piston at least half way exposed to inlet conduit 54 through the inlet hole 52 to speed the operation of the piston; the volume behind the piston can thereby fill more rapidly than if it had to fill through the clearance around the piston.

Figure 11:
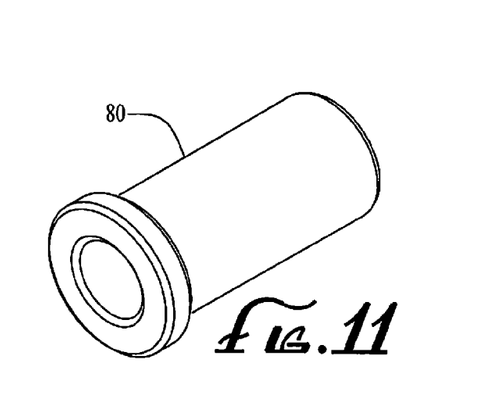
FIG. 11 is a right front perspective view of the piston guide 80 illustrated in FIG. 5.

The ejector piston 50, in its preferred form, is a total of 0.615 inches (15.621 mm) in length, including the 0.060 inch (15.24 mm) long rearward-extending nub, a head that is 0.180 inches (4.572 mm) long and a rod that is 0.375 inches (9.525 mm) long. Preferably, the nub diameter is 0.048 inches (1.2192 mm), the head diameter is 0.139 inches (3.5306 mm), and the rod diameter is 0.048 inches (1.2192 mm). A small clearance between the outer diameter of the rod and the internal diameter of the piston guide 80 (e.g., 0.002-0.003 inches (0.0508-0.0762 mm)) provides a clearance through which irrigation liquid can be delivered to the cutting edge of the punch during operation, as described below. As shown in FIG. 5, the piston rod 50b extends into one end of a generally tubular piston guide 80 (illustrated more clearly in FIG. 11), where it engages the rearward end of the ejector pin 46 as it is urged forwardly. The forward end portion of the piston guide preferably has an enlarged outer diameter in sealing contact with a seal 56.

A return spring 48 (FIG. 5) is captured between the rearward-facing end 80a of the piston guide 80 (FIG. 11) and the head 50a of the ejector piston 50 (FIG. 10) so that it is compressed as the piston moves the ejector pin 46 forwardly to eject an impacted follicular unit, and thereby returns the piston to its initial position once the hydraulic pressure behind the piston is sufficiently reduced via operator control or automatically after a period of time has elapsed since the beginning of the pulse if preferred by the equipment designer.

FIG. 15 is a side elevation view of the preferred ejector pin 46. The proximal end of the pin 46 had a head 46a of larger cross-section than the pin. The head has one or more flats that enable fluid to pass more easily around the head and flow through the piston guide 80 and into the punch. The head 46a further serves to provide a contact surface for the piston rod 50b (FIG. 10) and to limit the depth within the punch to which the ejector pin 46 can extend.

Because the preferred ejector pin 46 is not integral with the ejector piston 50, the reader will note that the return of the piston 50 to its initial position does not in itself return the pin 46. However, the distal end of the pin 46 has a head 46a of larger outer diameter than the internal diameter of the punch 42, limiting the depth to which the pin can extend into the punch. The length of the pin is dimensioned so that it cannot extend through the last millimeter or two nearest the cutting edge of the punch. Accordingly, the pin will not interfere with the gathering of hair follicle, even when the head 46a is in contact with the proximal end of the punch. Impacted grafts and debris, on the other hand, will push the freely moving pin 46 proximally, thereby moving the head 46a away from the proximal end of the punch and permitting the piston to urge the pin distally to eject the impacted graft and/or debris.

Figure 16:
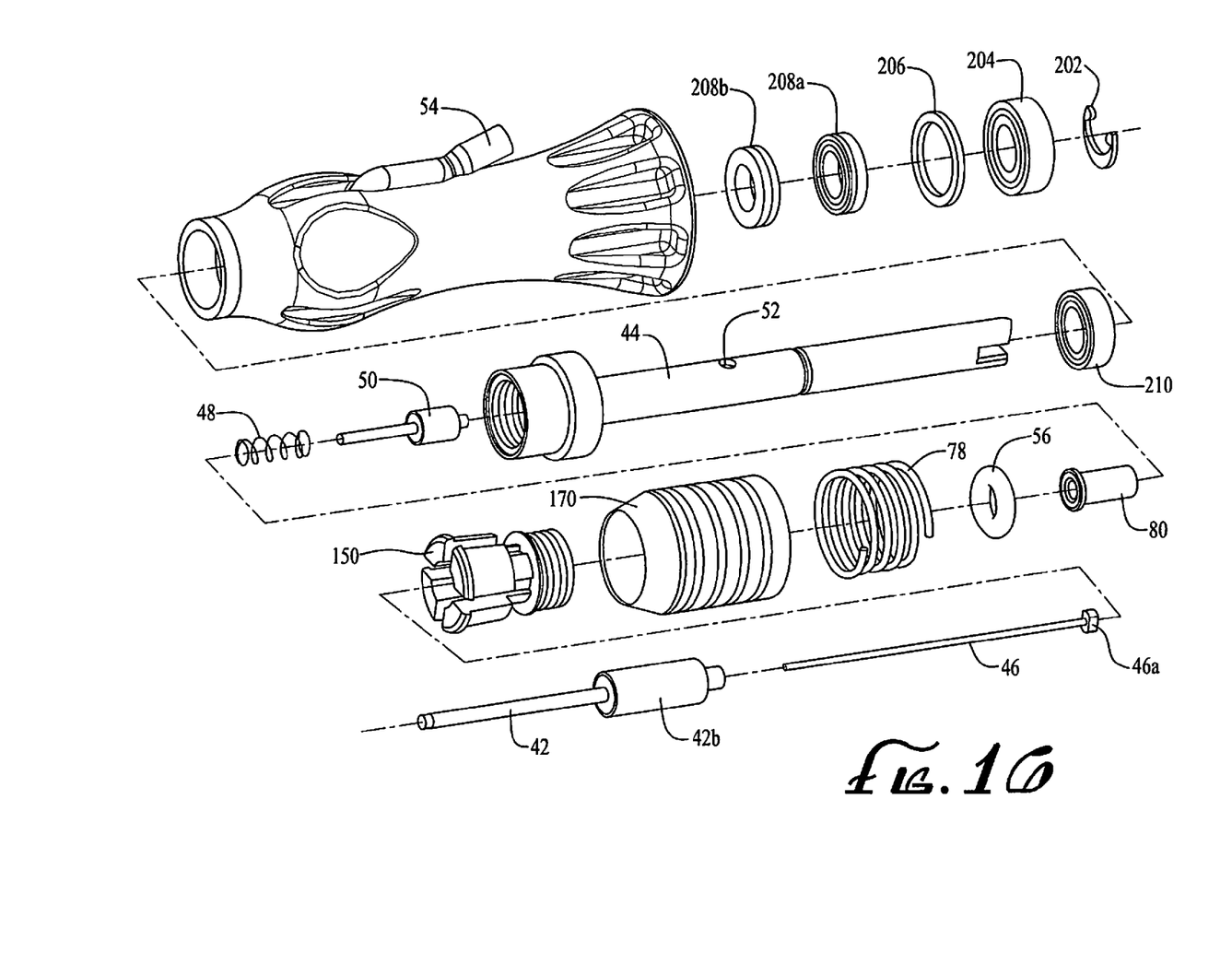
FIG. 16 is an explosion view of the currently preferred embodiment of a handpiece constructed in accordance with the invention.

FIG. 16 is an explosion view of the preferred embodiment further illustrating the preferred relative positioning and configurations of the various elements of the invention. In the embodiment illustrated in FIG. 16, a further modification is shown in that the coupling block 42b associated with the punch 42 has a substantially cylindrical exterior that is secured by the collet 150. The coupling block continues to have a greater outer dimension than the remainder of the punch body. The generally cylindrical exterior of the coupling block may result in less "wobble" as the punch rotates owing to slight differences that can occur when manufacturing coupling block having exterior of other shapes.

FIG. 16 also illustrates the placement of other preferred components used in assembling the preferred handpiece: snap ring 202, ball bearings 204, 210, seal backup spacer 206, and Teflon seals 208a,b.

In preferred operation, an electric motor causes the driveshaft 44 to rotate about axis 41 (FIG. 4) so that the driver socket coupling block and punch rotate about that axis as well. Irrigation fluid is introduced via inlet 54 by means of a pump that may conveniently be driven by the shaft-rotating motor or a separate motor. The irrigation liquid enters the handpiece via the irrigation ports 52, and leaks past the piston head 50a into the piston guide 80, nub 42d (FIG. 6), and punch 42 to irrigate the donor site. The leakage rate preferably provides about 1 tiny drop of irrigation fluid per second.

If a follicle unit becomes impacted within the punch, the pump speed is increased by operator-actuated means such as an operator-actuated foot pedal or handpiece button to create a flow rate in excess of the leakage rate, and a consequential build-up of hydraulic pressure on the rearward surface of the piston 50, urging it forward against return spring 48 to thereby clear the punch with the forwardly moving ejector pin 46.

Thus, the preferred configuration provides a pump that runs very slowly during the follicle extraction process to provide irrigation wherein the irrigating liquid leaks around the piston and out through the center of the punch, with the return spring 48 keeping the piston back, while for plug removal from the punch, the pump is run at or near full speed, overcoming the leakage and forcing the piston forward.

Other methods for increasing the pressure against the piston, either hydraulically, mechanically or electrically, can be utilized as well, and will be obvious to those of ordinary skill although the preferred embodiment uses the fluid used that is also used to irrigate the donor site during the follicle extraction procedure.

All components of the preferred handpiece are formed from stainless steel, except for the sealing rings which are formed from by a silicone rubber o-ring and Teflon shaft seals, so that the handpiece is preferably autoclavable. Accordingly, the irrigation fluid is safely delivered to the donor site and risk is minimized with respect to infection to the patient from bacteria that could be transferred to the punch and/or donor site from a non-sterile handpiece.

Although a liquid fluid is the preferred medium for ejecting the impacted grafts and/or debris from the punch lumen, air, gas, vapor or other medium may be used, and is within the scope of the invention.

The connection of the device to the punch might take any form, including but not limited to fluid and/or air sealed formats to facilitate the efficient delivery of liquid, vapor, air, or other gas from the device to and through the lumen of the punch and/or the punch's cutting edge.

It will also be understood that that the handpiece may be held and manually manipulated by a human operator or by a machine operating under human or microprocessor control, and that the term "handpiece" as used herein does not connote or denote the need for it to necessarily be grasped by a human hand.

Although a preferred punch, and variations thereof, were used in illustrating the functions of the embodiment, the use of any cutting device that has a lumen and a cutting end could be used without departing from the spirit of the invention.

Although a preferred embodiment of the present invention and its advantages have been described in detail above, it should be understood that various details, changes, substitutions and alterations will be apparent to those of ordinary skill in the art having the benefit of the foregoing specification. It is intended that all such variations be within the scope and spirit of the invention, and that the invention be solely defined by appended claims that shall be given the broadest allowable interpretation consistent with the Doctrine of Equivalents.

We claim:

1. A handpiece for follicular unit extraction comprising:
   a handpiece body extending along a generally central axis for holding a follicle punch having a cutting edge;
   a motor-driven driveshaft mounted within the handpiece body for rotation about the axis for rotating the follicular punch when said punch is held by the handpiece;
   a fluid path carried by the handpiece for conducting a fluid from a source external to the handpiece into the lumen of the follicle punch held by the handpiece for delivery of the fluid to the cutting edge of the follicle punch;
   an ejector pin positioned within the fluid path of the handpiece for axial movement from a retracted position to a deployed position within the follicle punch when the punch is held by the handpiece so as to eject an impacted graft or debris from the punch's interior;
   operator-controlled means for moving the pin axially between the retracted and deployed positions;
   an ejector piston positioned in the fluid path and having a distal end portion for moving the ejector pin from said retracted position to said deployed position, and further having a proximal face positioned upstream in said fluid path from said distal end portion and configured to be responsive to the force of flowing fluid in said fluid path; and
   a biasing component for preventing movement of the ejector piston when the force of the flowing fluid is less than an activating level.

2. The handpiece of claim 1 wherein
   the ejector pin is positioned within the fluid path for axial movement towards the cutting edge in response fluid pressure within the fluid path to clear the interior of a punch held by the handpiece, and
   the handpiece includes a return spring positioned to oppose said axial movement by the ejector pin, and exhibiting a force that substantially prevents such movement until said fluid pressure exceeds a threshold value.

3. The handpiece of claim 1 further including a follicle punch having a generally tubular body defined between an inner wall and an outer wall, said follicle punch being removably secured within the handpiece body in substantial axial alignment with said ejector pin to permit the ejector pin to move axially within the punch between said retracted position and said deployed position.

4. The handpiece of claim 3 wherein the handpiece body includes an inlet port, and the fluid path within the handpiece is defined by a path that extends from the inlet port, around the ejector piston and through the path defined by the inner wall of the punch and ejector pin, with the fluid exiting from the punch at its cutting end.

5. The handpiece of claim 4 wherein the fluid path is dimensioned to limit the volumetric rate of fluid exiting from the cutting end of the punch.

6. The handpiece of claim 1 including
a generally tubular follicle punch removably secured within the handpiece body in substantial axial alignment with said ejector pin and positioned to permit the ejector pin to move axially within the punch between said retracted position and said deployed position.

7. The handpiece of claim 6 wherein the follicle punch includes a cutting edge at its distal end region and a coupling block region proximal to the distal end region, the coupling block region having one or more larger outside dimension than the corresponding one or more outside dimensions of the punch at its distal end.

8. The handpiece of claim 7 wherein the coupling block includes a nub at its proximal end.

9. The handpiece of claim 8 further including a sealing ring sealingly circumventing the nub.

10. A follicular unit extraction tool comprising:
a generally tubular handpiece body extending between proximal and distal ends for holding in its distal end region a follicle punch having a cutting edge, said handpiece body having a first inlet port for coupling the interior of the handpiece to a source of fluid;
a generally tubular follicle punch removably secured within the distal end region of the handpiece and extending distally therefrom along an axis, said punch terminating in a cutting edge at its distal end;
a motor-driven driveshaft mounted within the handpiece body for rotation about the axis for rotating the follicular punch, the driveshaft having a generally tubular distal portion and a second inlet port extending between the exterior and interior of said tubular portion for conducting fluid entering the handpiece into the interior of the driveshaft;
an ejector piston positioned within the tubular portion of the drive shaft distally of the second inlet port, and axially movable between a relatively proximal retracted position and a relatively distal deployed position;
an ejector pin supported within the tubular portion of the driveshaft distally of the ejector piston and positioned to move axially within the punch distally towards and proximally away from a distal deployed position;
the clearance between the ejector piston and driveshaft interior, and the clearance between the ejector pin and punch interior, defining a fluid path for conducting fluid entering the handpiece and drive shaft via the first and second inlet ports so that the fluid exits the punch at its cutting edge,
the clearance between the ejector piston and driveshaft interior, and the clearance between the ejector pin and punch interior, limiting the quantity of fluid exiting the punch;
bias means for retaining the piston at its proximal position unless the pressure of the fluid entering the driveshaft exceeds a threshold value,
the piston thereby responding to fluid pressure in excess of the threshold value by moving distally to contact the pin and urge the pin axially to its deployed position within the punch to clear the punch interior of impacted matter,
the piston thereby returning to its proximal position when the fluid pressure within the driveshaft falls below the threshold value, and
means for selectively increasing the fluid pressure within the driveshaft by increasing the entry rate of fluid entering the first inlet port beyond the limit imposed by said clearances.

* * * * *